United States Patent [19]

Hausheer

[11] Patent Number: 6,075,053
[45] Date of Patent: Jun. 13, 2000

[54] METHOD OF REDUCING OR REVERSING NEUROPATHY

[75] Inventor: Frederick Herman Hausheer, Boerne, Tex.

[73] Assignee: BioNumerik Pharmaceuticals, Inc., San Antonio, Tex.

[21] Appl. No.: 09/246,471

[22] Filed: Feb. 9, 1999

[51] Int. Cl.⁷ .................................................. A61K 31/185

[52] U.S. Cl. ............................................................ 514/578

[58] Field of Search ............................................... 514/578

[56] References Cited

U.S. PATENT DOCUMENTS 5,262,169  11/1993  Sauerbier et al. ........................ 424/465
5,919,816   7/1999  Hausheer et al. ........................ 514/449

*Primary Examiner*—Raymond Henley, III
*Assistant Examiner*—Jennifer Kim
*Attorney, Agent, or Firm*—Thomas J. Dodd

[57] ABSTRACT

This invention relates to a method of treating patients afflicted with peripheral neuropathy. The method includes administering to a patient in need of treatment an effective amount of a thiol or reducible disulfide compound according to the formula set forth in the specification.

5 Claims, No Drawings

METHOD OF REDUCING OR REVERSING NEUROPATHY

FIELD OF THE INVENTION

This invention relates to methods of reducing or reversing neuropathy, and will have application to methods of reducing peripheral neuropathy which has been induced by chemotherapeutic and other agents.

BACKGROUND OF THE INVENTION

One of the many undesirable side effects of certain antineoplastic agents is neurotoxicity. In particular, platinum complex drugs, epipodophyllotoxins, vinca alkaloids (particularly Vincristine), taxanes, some DNA alkylating agents, antifolates, and antineoplastic antibiotics all have been known to mediate peripheral neuropathy in a significant percentage of patients to whom the drugs are administered.

Peripheral neuropathy may also be mediated by a number of other diseases and conditions. Some of the causes include alcoholism, diabetes mellitus, certain B-vitamin deficiencies, inherited conditions, and others. Many of these neuropathies are reversible if treated promptly.

Though not typically a life-threatening condition, peripheral neuropathy impacts negatively on the quality of life for the patient. Peripheral neuropathy often manifests in symptoms of numbness, pain, paralysis, tics, twitching, and other uncontrollable reflex actions, particularly in the limbs. Many patients afflicted with this condition are unable to perform simple everyday tasks like getting dressed, driving an automobile, personal grooming, feeding oneself, and other relatively simple tasks.

Unless the neurotoxic effects of the antineoplastic agent are reversed quickly, the condition can, and often does, become a permanent disability. Neural cells divide slowly, and unless the cytotoxic effects of the antineoplastic agent can be stemmed in these cells, neuronal cell death occurs with the resultant neuropathic manifestations.

The neurotoxic effects of platinum based agents are generally irreversible and incurable. Patients afflicted with platinum mediated neuropathy often become permanently disabled, unable to work, or even to function productively in society. Also, the psychological trauma associated with such a condition is oftentimes devastating to the patient.

Currently, there is little that can be done to reduce the risks of neuropathy in patients undergoing chemotherapy, particularly when platinum complexes are involved. Amifostine (Ethyol®) has been administered in efforts to reduce platinum complex toxicity, but has shown inconsistent efficacy and also mediates independent undesirable toxic events (hypotension, nausea and vomiting are commonly observed in patients receiving Amifostine) in a significant percentage of patients. Amifostine has also been shown to be a tumor protectant in some studies, which can adversely affect the success of the treatment.

Mesna (sodium 2-mercaptoethene sulfonate) and dimesna (disodium 2,2'-dithiobis ethane sulfonate) are known therapeutic compounds which have heretofore demonstrated a wide variety of therapeutic uses. Both mesna and dimesna have been shown to be effective protective agents against certain specific types of toxicity associated with the administration of cytotoxic drugs used to treat patients for various types of cancer. In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses that may be needed can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The structures of both mesna and dimesna are shown below as Formula I and Formula II respectively.

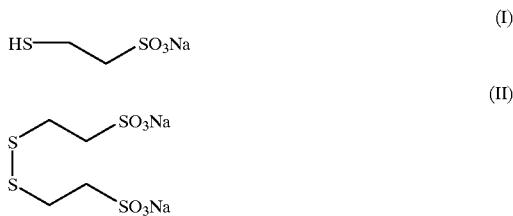

As is well known, dimesna is a dimer of mesna, with the optimum conditions for oxidation occurring in the slightly basic (pH ~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with cisplatin or carboplatin.

Mesna and dimesna, as well as some analogues of these compounds, have excellent toxicity profiles in mammalian species. In fact, dimesna has been administered intravenously to mice and dogs in doses higher than the accepted oral $LD_{50}$ for common table salt (3750 mg/kg), with no adverse effects. Dimesna has also been administered to humans in doses exceeding 15 g/m$^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well-known in the art. One such method involves the two-step, single pot synthetic process for making dimesna and like compounds of the following formula:

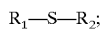

wherein:

R is hydrogen, X-lower alkyl, or X-lower alkyl-$R_3$;

$R_2$ is -lower alkyl-$R_4$;

$R_3$ and $R_4$ are each individually $SO_3M$ or $PO_3M_2$;

X is absent or X is sulfur; and

M is an alkali metal.

The process essentially involves a two step single pot synthetic process which results in the conversion of an alkenyl sulfonate salt or acid to the desired formula I compound. The process in the case of mesna is a single step process which converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well-known and documented in the prior art, may be employed to make either mesna or dimesna, or derivatives and analogues thereof.

SUMMARY OF THE INVENTION

This invention involves the administration of an effective amount of a compound of formula I, below, for treating patients afflicted with reversible peripheral neuropathy.

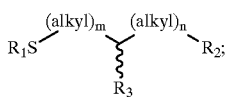

(I)

wherein:

$R_1$ is hydrogen, lower alkyl or

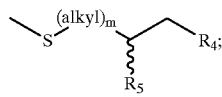

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

Effective amounts of the formula I compounds to be administered according to the method of this invention vary, and depend on the severity and duration of the neuropathy.

Accordingly, it is an object of this invention to provide for a method of safely and effectively treating peripheral neuropathy.

Another object is to provide a method of treating peripheral neuropathy by administration of a thiol or reducible disulfide to the patient in need of treatment.

Other objects will become apparent upon a reading of the following description.

DESCRIPTION OF THE PREFERRED EMBODIMENTS

The preferred embodiments herein described are not intended to be exhaustive nor to limit the invention to the precise form disclosed. They are chosen and described to explain the principles of the invention, and its application and practical use to best enable others skilled in the art to follow its teachings.

The method of this invention involves the administration of an effective amount of a formula I compound to a patient suffering from peripheral neuropathy. Administration may be either oral or parenteral.

The effective amount of the formula I compound will necessarily depend upon the degree of the neuropathy. Since the formula I compounds are essentially nontoxic, large amounts can be safely administered. The preferred dosage to treat peripheral neuropathy ranges from 0.1 mg/kg of body weight up to 3,000 mg/kg. The more severe the neuropathy and associated neuronal degradation, the more formula I compound should be administered to provide an effective response.

Administration is preferably through parenteral or oral routes. For parenteral administration, the formula I compound is dissolved in a suitable solvent, most preferably water, to produce a solution which may be injected. One or more pharmaceutically acceptable excipients may also be added to provide for an elegant formulation.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a swallowable container such as a gelatin capsule or the like.

The formula I compounds work to detoxify metal complexes or free radicals by substituting a thiol moiety for a toxic free radical or other nucleophilic moiety.

Administration of the formula I compound should be made as soon as possible following diagnosis of neuropathy. Preferred initial dose is between 20 mg/kg and 500 mg/kg.

Other accepted methods of treatment may also be combined with the administration of the formula I compound. In particular, if the neuropathy is due to poisoning which is recent in nature, emesis-inducing drugs should be given in attempts to lower the amount of absorbed poison. The patient may then be dosed with the formula I compound to neutralize any of the poison which may have already absorbed.

It is understood that the above description is in no way limiting of the invention, which may be modified within the scope of the following claims.

What is claimed is:

1. A method of treating a neuropathy in a patient, said method comprising administering an effective amount of a compound of formula I:

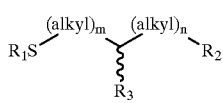
(I)

wherein:

$R_1$ is hydrogen, lower alkyl or

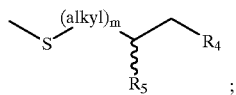
;

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

2. The method of claim 1 wherein the effective amount of the formula I compound administered is from 0.1 mg/kg of body weight to 3,000 mg/kg of body weight.

3. The method of claim 1 wherein the compound is administered orally.

4. The method of claim 1 wherein the compound is administered parenterally.

5. The method of claim 1 wherein the compound is administered following the administration of emesis-inducing agents.

* * * * *